(12) United States Patent
Bienenstock

(10) Patent No.: US 9,517,037 B2
(45) Date of Patent: Dec. 13, 2016

(54) SINGLE PHOTON EMISSION COMPUTED TOMOGRAPHY IMAGING METHOD

(71) Applicant: Elazar A. Bienenstock, Toronto (CA)

(72) Inventor: Elazar A. Bienenstock, Toronto (CA)

( * ) Notice: Subject to any disclaimer, the term of this patent is extended or adjusted under 35 U.S.C. 154(b) by 0 days.

(21) Appl. No.: 14/877,142

(22) Filed: Oct. 7, 2015

(65) Prior Publication Data

US 2016/0022229 A1    Jan. 28, 2016

Related U.S. Application Data

(62) Division of application No. 13/792,632, filed on Mar. 11, 2013, now Pat. No. 9,173,625.

(30) Foreign Application Priority Data

Apr. 30, 2012 (CA) ..................................... 2775869
Nov. 5, 2012 (CA) ..................................... 2794281

(51) Int. Cl.
*A61B 6/00* (2006.01)
*A61B 6/03* (2006.01)
*A61K 51/02* (2006.01)

(52) U.S. Cl.
CPC ............... *A61B 6/037* (2013.01); *A61B 6/486* (2013.01); *A61B 6/503* (2013.01); *A61B 6/504* (2013.01);
(Continued)

(58) Field of Classification Search
CPC ... A61B 2090/392; A61B 6/037; A61B 6/486; A61B 6/503; A61B 6/504; A61B 6/507; A61B 6/5235; A61K 51/02
See application file for complete search history.

(56) References Cited

U.S. PATENT DOCUMENTS 7,848,557 B2   12/2010   Kadrmas et al.
8,000,773 B2    8/2011   Rousso et al.
(Continued)

FOREIGN PATENT DOCUMENTS

WO   2011070465 A2   6/2011

OTHER PUBLICATIONS

Berman et al., "Stress Thallium-201/Rest Technetium-99m Sequential Dual Isotope High-Speed Myocardial Perfusion Imaging", Cardiovascular Imaging, (Mar. 2009), vol. 2, No. 3, pp. 273-282.
(Continued)

*Primary Examiner* — Ruth S Smith
(74) *Attorney, Agent, or Firm* — The Webb Law Firm

(57) ABSTRACT

A SPECT diagnostic method of performing myocardial perfusion imaging on a patient, consisting of
(A) administering a rest radiotracer to the patient while the patient is at rest; then
(B) when the rest radiotracer is fixed in a heart of the patient, scanning the heart to obtain rest heart pumping ability information;
(C) scanning the heart of the patient to obtain a rest perfusion image;
(D) administering a stressing agent to the patient to place the patient's heart under stress;
(E) scanning the heart of the patient to obtain stress heart pumping ability information; then
(F) administering a stress radiotracer while the heart of the patient is under stress; then
(G) when the stress radiotracer is fixed in the heart, scanning the heart to obtain a stress perfusion image.

9 Claims, 3 Drawing Sheets

(52) U.S. Cl.
CPC ............ *A61B 6/507* (2013.01); *A61B 6/5235* (2013.01); *A61K 51/02* (2013.01); *A61B 2090/392* (2016.02)

(56) References Cited

U.S. PATENT DOCUMENTS

| | | |
|---|---|---|
| 2002/0188170 A1 | 12/2002 | Santamore et al. |
| 2010/0021378 A1 | 1/2010 | Rousso et al. |
| 2010/0104505 A1 | 4/2010 | O'Connor |
| 2012/0245460 A1* | 9/2012 | Slomka .............. A61B 5/02755 600/425 |

OTHER PUBLICATIONS

Fallahi et al., "Single Tc99m Sestamibi injection, double acquisition gated SPECT after stress and during low-dose dobutamine infusion: a new suggested protocol for evaluation of myocardial perfusion", Int. J. Cardiovasc. Imaging (2008), vol. 24, pp. 825-835.

Henzlova et al., "ANSC Imaging Guidelines for Nuclear Cardiology Procedures", Journal of Nuclear Cardiology, (2009).

Herzog et al., "Nuclear Myocardial Perfusion Imaging with a Cadmium-Zinc-Telluride Detector Technique: Optimized Protocol for Scan Time Reduction", The Journal of Nuclear Medicine, (Jan. 2010), vol. 51, No. 1, pp. 46-51.

Husain, "Myocardial Perfusion Imaging Protocols: Is There an Ideal Protocol?", J Nuclear Med Technol. (2007), vol. 35, pp. 3-9.

Slomka et al., "New Imaging Protocols for New Single Photon Emission CT Technologies", Curr. Cardiovasc. Imaging Rep., (2010), vol. 3, pp. 162-170.

\* cited by examiner

SINGLE PHOTON EMISSION COMPUTED TOMOGRAPHY IMAGING METHOD

CROSS REFERENCE TO RELATED APPLICATIONS

This application claims the benefit of U.S. Utility patent application Ser. No. 13/792,632 filed Mar. 11, 2013, which claims the benefit of CA 2794281 filed on Nov. 5, 2012 and CA 2,775,869 filed on Apr. 30, 2012, and is incorporated herein by reference.

FIELD OF THE INVENTION

This invention is directed to the field of SPECT, and in particular, to the field of myocardial perfusion imaging.

BACKGROUND OF THE INVENTION

Nuclear medicine is a field of medicine concerned with the use of radiation for diagnostic purposes. Single Photon Emission Computed Tomography (referred to in this specification as "SPECT"), a branch of nuclear medicine, involves directly measuring gamma rays emitted by radionuclides administered to a patient to produce slice-like images of the patient. "Tomography" refers to the production of slice-like images, or tomograms. Computerized Tomography (CT) refers to the use of computer processing to derive the tomogram.

Typically, in SPECT procedures, radiopharmaceuticals (otherwise known as radioactive tracers or radiotracers) are administered to patients. Radiopharmaceuticals are generally compounds consisting of radionuclides (i.e. radiation-emitting atoms), combined with pharmaceuticals or other chemical compounds. In some cases, such as with Thallium-201, the same particle is simultaneously the radionuclide and pharmaceutical. Unlike positron emission tomography (PET) which uses small radionuclides with half-lives of just over a minute to under 2 hours, SPECT involves the use of radionuclides whose half-life is several hours to days long, long enough to clinically localize or become fixed in specific organs or cellular receptors. In these circumstances, it is possible to acquire important diagnostic information by obtaining images created from the radiation emitted by the radiopharmaceutical.

One frequently-performed SPECT diagnostic procedure is myocardial perfusion imaging (MPI). Approximately ten million such scans are performed in the U.S. annually. For MPI, the patient is injected with a radioactive tracer which collects in, and becomes fixed in, the heart muscle. The localization of the tracer within the heart is dictated by the blood flow through the coronary arteries. These are the blood vessels that supply blood directly to the heart muscle, the myocardium. Therefore, MPI provides important information about the blood flow through the coronary arteries to the heart muscle. Thus, MPI can be used to diagnose serious and potentially fatal heart conditions such as coronary artery disease.

A typical MPI procedure involves a rest, or baseline scan and a stress scan, commonly on the same day, leading with the rest scan. These two scans are employed because important information is provided by the difference in blood flow demonstrated by the two scans. For example, certain coronary arteries of a particular patient may be partially occluded. However, at rest, the coronary artery has the capacity to dilate to offset the occlusion, and a rest scan alone may not show any decreased blood flow through the heart.

On the other hand, under stress, the coronary arteries will dilate to their maximum extent to handle the increased blood flow. Under such conditions, dilation of the diseased coronary artery will not be enough to offset the partial occlusion, with the result that the decreased blood flow will become apparent from the stress scan.

In addition to being used to look for heart defects reflected by anomalies in blood distributions throughout the heart muscle, MPI is used for obtaining information about heart pumping ability, preferably including analyzing heart wall motion and left ventricle ejection fraction. Regarding wall motion, MPI can be used to determine whether there are any abnormalities in the motion of the heart walls, and in particular, the motion of the walls of the left ventricle.

Left ventricle ejection fraction is a term that describes the percentage of blood in the left ventricular cavity that is ejected when the left ventricle contracts to pump blood out of the heart to the body. An ejection fraction that is too low can be indicative of heart disease. Also, the ejection fraction's actually dropping from the rest scan to the stress scan can be indicative of serious heart disease.

For the MPI stress scan, stress is usually created either through exercise, or through the administration of a stress pharmaceutical. A typical order of events when a patient undergoes an MPI scan is as follows. The patient is injected with a radioactive tracer while sitting at rest. Approximately 30-45 minutes later, the patient undergoes the MPI rest scan. The 30-45 minute waiting time has traditionally been needed because some of the tracer typically accumulates in the liver and bowels, and the radiation from that accumulation has been understood to interfere with scanning of the heart. The delay was needed for the tracer in the liver and bowels to dissipate. The rest scan provides information about the resting blood flow within the heart muscle, the resting size of the left ventricle, and the resting left ventricle ejection fraction.

Then, the patient leaves the scanning area to be stressed, returning later for the stress scan.

If the stress is induced by exercise, the patient runs on the treadmill or does some other exercise adequate to produce the required stress. If a stress pharmaceutical is used, then the patient receives the stress pharmaceutical, usually lying down, but sometimes sitting, or even walking on a treadmill. A common stress pharmaceutical is dipyridamole, which is typically infused over about four minutes. Next, at either peak exercise, or at the time of maximal effect of the stress pharmaceutical, the radioactive tracer is administered, and becomes fixed in the heart according to the distribution of the blood flow at the time of the injection.

Typically, the patient returns at least 30-45 minutes after the administration of the stress radioactive tracer in order to be scanned. In practice, the delay is often 2-4 hours because of scanning backlogs that develop through the day. The stress scan reflects relative myocardial blood flow distribution that prevailed at peak stress, that is, at the time of the stress injection. The same scan is used to assess the size and pumping ability of the heart after stress. The stress scan is compared with the rest scan to determine whether there are stress-induced blood flow defects in the heart muscle, whether the heart becomes dilated, and whether it has developed reduced pumping ability, indicated by either a drop in ejection fraction, or visually assessed local wall motion abnormalities.

A problem with this typical protocol is that the information provided after the stress scan, in relation to heart size and pumping ability, is unreliable. Specifically, the stress scan is typically conducted well after the actual peak stress on the heart. There is plenty of time available for the heart to recover and return to its normal size and pumping ability. This delay does not necessarily adversely affect the acquisition of information regarding myocardial blood perfusion in the heart, because the radioactive tracer remains fixed in the heart according to blood flow through the heart during peak stress. However, because the stress scan takes place at least 30-45 minutes after peak stress, but usually after a few hours, it discloses heart size, wall motion and ejection fraction of the heart as it is at least 30-45 minutes after stress. The result is that there are many patients who have enlarged hearts or reduced pumping ability when their hearts are under stress, but whose heart recovers within 30-45 minutes or more, and whose conditions are therefore not detected.

SUMMARY OF THE INVENTION

Therefore, what is desired is a method that facilitates a more accurate assessment of heart pumping ability under stress. Preferably, the time and effort needed to complete the rest and stress scan and the amount of radiation imparted to the patient are reduced, with the quality of the scan being improved.

According to the present invention, there is provided a SPECT diagnostic method of performing myocardial perfusion imaging on a patient, the method comprising the steps of:

(A) administering a rest radiotracer to the patient while the patient is at rest; then (B) when the rest radiotracer is fixed in the heart of the patient, scanning the heart to obtain rest heart pumping ability information;

(C) scanning the heart of the patient to obtain a rest perfusion image;

(D) administering a stressing agent to the patient to place the patient's heart under stress;

(E) scanning the heart of the patient to obtain stress heart pumping ability information; then (F) administering a stress radiotracer while the heart of the patient is under stress; then (G) when the stress radiotracer is fixed in the heart, scanning the heart to obtain a stress perfusion image.

In another aspect of the invention, there is provided a SPECT diagnostic method of performing myocardial perfusion imaging on a patient, the method comprising the steps of:

(A) administering a stressing agent to the patient to place the patient's heart under stress; then (B) administering a stress radiotracer while the heart of the patient is under stress;

(C) when the stress radiotracer is fixed in the heart, immediately scanning the heart to obtain a stress perfusion image and stress heart pumping ability information;

(D) preferably without moving the patient, administering a rest radiotracer to the patient once the patient is at rest;

(E) when the rest radiotracer is fixed in a heart of the patient, scanning the heart to obtain rest heart pumping ability information and a rest perfusion image.

BRIEF DESCRIPTION OF THE DRAWINGS

Reference will now be made, by way of example only, to the figures which illustrate the preferred embodiment of the invention, and in which.

DETAILED DESCRIPTION OF THE PREFERRED EMBODIMENTS

In this specification, "stress" refers to the induced dilation of the coronary arteries of a patient. "Rest" refers to the absence of stress.

Figure 1:
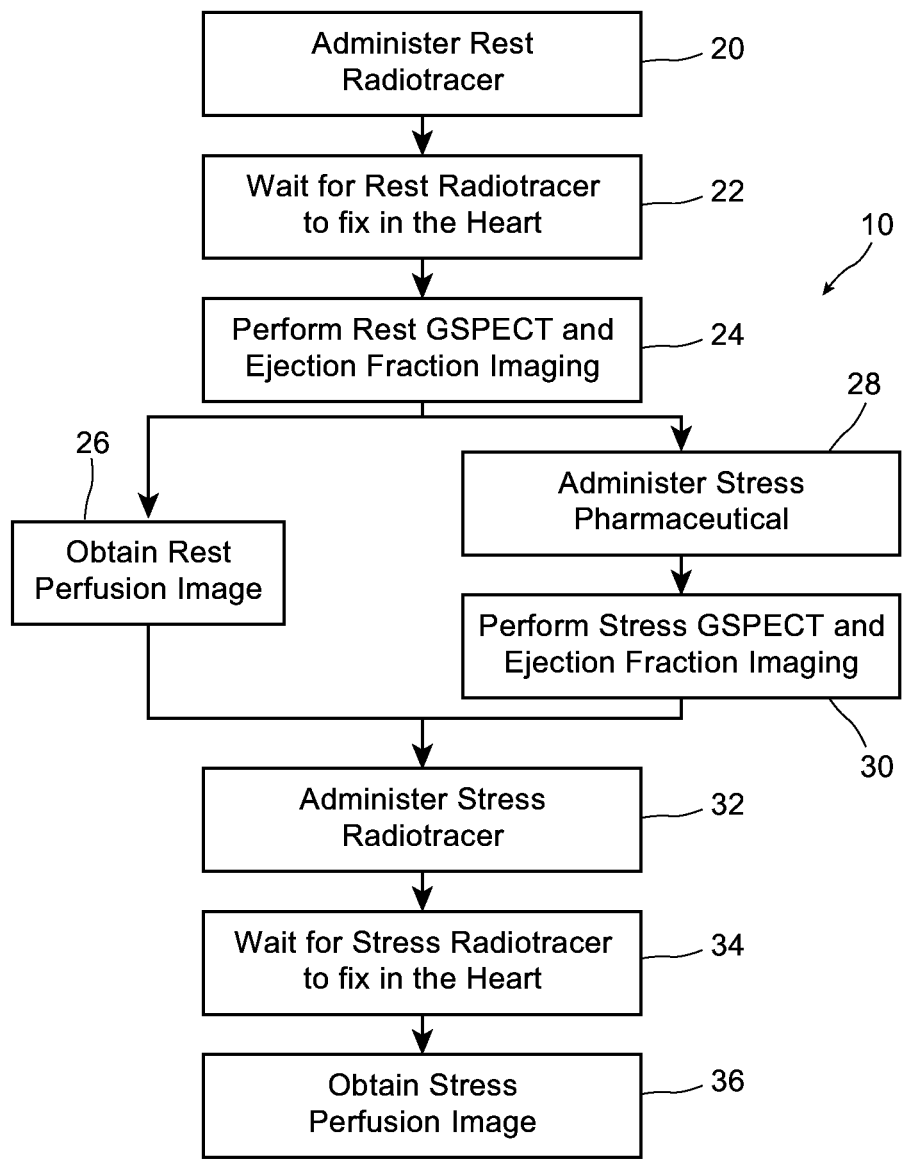
FIG. 1 is a flowchart showing the sequence of steps comprising the preferred embodiment of the method.

Referring now to FIG. 1, the steps of the preferred SPECT diagnostic method of performing MPI on a patient are shown. In the SPECT diagnostic method described herein, the patient is positioned appropriately relative to the SPECT camera that will be used to scan the patient and obtain images.

The technician or medical professional attending to the patient then performs the steps of the method. The first step 20 of method 10 comprises administering the rest radiotracer to the patient while the patient is at rest. The administration of the rest radiotracer injection may be done before or after the patient is placed under the SPECT camera. The technician then allows enough time to pass for the rest radiotracer to become fixed in the heart of the patient (step 22). Once the rest radiotracer is fixed, the patient's heart is scanned (step 24) to obtain rest heart pumping ability information. Most preferably, the heart pumping ability information comprises both wall motion information, and left ventricle ejection fraction information. Most preferably, ejection fraction is calculated by obtaining the end systolic volume and end diastolic volume of blood in the left ventricle. Wall motion and ejection fraction information are obtained by gating the study according to the ECG rhythm, and binning the information into components grouped according to their temporal position within the cardiac cycle. This is called Gated SPECT, or GSPECT. Wall motion is visually assessed by the reporting physician viewing the GSPECT image information in cine mode. Meanwhile, a computer uses the GSPECT information to calculate ejection fraction, defined as (VED−VES)/VED, where VES is end systolic volume, and VED is end diastolic volume. Because GSPECT does not require the same high-photon-count, statistically smooth image as the perfusion scan, it may be completed in less time than the perfusion scan.

Next, at step 26, the heart of the patient is scanned to obtain a rest perfusion image, that is, an image showing the blood flow through the heart when the patient is at rest. Then, preferably without moving the patient, who remains under the camera, the stressing agent (for placing the heart of the patient under stress, or dilating the coronary arteries) is administered to the patient (step 28). Once the stressing agent (typically a stress pharmaceutical) has brought the patient's heart to an adequate level of stress, the heart of the patient is scanned to obtain stress heart pumping ability information (step 30). Preferably, the patient is kept stationary from the commencement of the rest perfusion scan through the completion of all of the rest and stress scans.

It will be appreciated that there are a number of stress pharmaceuticals used in MPI, including dipyridamole, dobutamine, adenosine and adenosine receptor agonists, such as regadenoson, with dipyridamole being very commonly used. Non-pharmaceutical stressing agents may also be employed. These include but are not necessarily limited to "cold presser testing" (immersing a hand in very cold water), mental stress (such as math exercises), bicycle exercise and handgrip exercise. Additional methods are being developed. Any safe and effective stressing agent may be used if it does not interfere with the execution of the present diagnostic method.

Most preferably, the stressing agent used will be one which permits the patient to remain stationary from the beginning of the rest perfusion scan through the end of the stress perfusion scan. Thus, stress pharmaceuticals are most preferred as stressing agents, because they are safe, effective, easily available, commonly used, and allow the patient to remain essentially stationary while the heart is placed under stress.

The stress radiotracer is administered while the heart of the patient is under stress (step 32), so that the stress radiotracer will fix in the heart in accordance with the relative blood flow distribution in the heart under stress conditions. Next, the nuclear medicine technologist waits (typically about 1 minute) for the stress radiotracer to fix in the heart (step 34). Once the stress radiotracer is fixed in the heart, the heart is scanned to obtain a stress perfusion image (step 36).

It will be appreciated that it is not necessary to complete rest perfusion imaging (step 26), before starting to induce stress (usually with a pharmaceutical) (step 28). Rather, to save time, it is possible for the stressing agent to be administered after step 24 is complete but while the rest perfusion scan is still being performed. Specifically, at steps 26, 28 and 30, the only radiotracer that has been administered to the patient and fixed in the patient's heart is the rest radiotracer. In the preferred form of the present method, the GSPECT for rest and then stress is performed using the rest radiotracer. Thus, it is possible for the rest perfusion scan and the stress GSPECT to be obtained at the same time, or at least, to overlap in time. In summary, only the rest radiotracer injection and resting GSPECT must be completed before the stressing agent is administered. Once the rest radiotracer is injected and rest GSPECT imaged, the stress agent can be administered and stress GSPECT can be acquired without interfering with, or preventing the ongoing collection of, the rest perfusion image. In some embodiments, if desired, obtaining the rest perfusion image can further continue right through the administration of the stress radiotracer and the obtaining of the stress perfusion image, as described below.

It will further be appreciated that the present method provides better information about the heart's pumping ability under stress as compared with prior art methods. Under typical prior art methods, the patient typically receives a stress pharmaceutical, and then a stress radiotracer at peak stress. Following that, under the prior art methods, the patient leaves the scanning area and waits at least 30-45 minutes, and often 2 to 4 hours, for the stress scan. Thus, wall motion and ejection fraction are measured well after peak stress, and often do not accurately reflect actual stress wall motion and ejection fraction. In turn, this can result in heart conditions, which should be caught and treated, being missed.

By contrast, in the preferred embodiment of the present method, the stress GSPECT is performed using radiation emitted by the rest radiotracer. Thus, there is no forced delay between the stressing of the heart and the stress GSPECT, as in the prior art methods. Rather, the stress GSPECT can be done at or near the time of peak stress for the patient's heart, and will therefore accurately convey information about the pumping ability of the heart under stress, including the wall motion under stress, and the ejection fraction under stress.

Another advantage of this method, in which the patient preferably remains in the scanning position and does not move from the beginning of the rest scan to the end of the stress scan, is the convenience of eliminating the extra steps of getting the patient on and off the imaging table. It should be noted that positioning the patient for the second time can be much more difficult than the first time because the technologist must attempt to recreate the exact same bed and scanner positions relative to the patient and heart as the first scan. Therefore eliminating the need to recreate identical conditions for the two studies is beneficial. This is also desirable from a diagnostic perspective, since the stress and rest images will generally be perfectly aligned and there will be no shifting of body parts or internal organs between scans. This, in turn will eliminate, or minimize, improper alignment which interferes with both the computerized quantitative analysis (commonly referred to in the industry as the bull's-eye plot) and visual interpretation. It will also eliminate, or minimize the problem of variable reconstruction artifacts. Image processing may be done in one step, with changes made by the technologist on one of the stress, or rest studies automatically mirrored on the other, saving on labour and preventing user error.

Furthermore, for 1-day protocols (a prior art method), it is common in the art for the stress and rest radiotracers to be the same (e.g. Technetium-based radiopharmaceutical), with the stress radiotracer being administered at roughly three times the dose of the rest radiotracer. The intention is that any stress-induced defect would be apparent despite residual radioactivity from the rest radiotracer, because of the higher dosage of the stress radiotracer, and its correspondingly greater radioactivity. In the preferred form of the present method, because the patient is stationary and the rest and stress images aligned, the low-count first (generally rest) image can be subtracted from the high count second (generally stress) image to produce a refined second perfusion image that has better lesion contrast and is thus more reliable. A numerical analogy would be as follows; If normal activity is defined as 100% and there was a 50% defect on the stress study, and residual activity from the normal rest scan added approximately 20% (with small natural local variations throughout the heart), then activity in the heart would be 120%, activity in the defect area would be 70% and the difference would be 50%. This 50% difference represents the severity of the defect. Therefore, the contrast of the severity of the defect would be 50/120, which is less than 50/100. By correctly subtracting the 20% confounding residual resting activity from the stress scan in both the normal area and in the defect area, the intensity of the defect is restored to 50/100. In turn, being able to subtract the first study from the second study should allow a smaller ratio between higher and lower radiotracer doses, with the result that less radioactivity is imparted to the patient. Subtraction may also facilitate simultaneous dual imaging (SDI) as described below. It will be appreciated that such subtraction can be done either on the raw images that are obtained by the camera, or on the tomographic images created by SPECT reconstruction.

Meanwhile, substantial advantages will accrue to the patient as well. In the preferred embodiment of the present invention, the entire study (rest and stress) may be completed in 20 minutes or less, particularly if newer faster cameras are used. Hours-long waits between scans would thus be practically eliminated. Furthermore, the technologist performing the scans will find it more convenient not to have to position the patient a second time, with all the inherent difficulties of trying to recreate the same scan position as for the first study. Also, manpower requirements are decreased and streamlined by allowing the scanning technologist, who must remain in the room with the patient anyway, to also participate in the administration of the stressing agent, virtually eliminating the need for an additional stressing technologist.

Those skilled in the art will appreciate that there are a variety of different radiotracers that can be used in MPI scanning. The most common is radiopharmaceutical based on Technetium-99m ("Tc", "99m-Tc" or "technetium"), an isotope of Technetium that, for use as a radiotracer, is combined with a carrier pharmaceutical. Currently available carrier pharmaceuticals are Sestamibi and Tetrofosmin Teboroxime is not currently commercially available, due to its rapid myocardial clearance. However, with the advent of new, faster, CZT cameras, Teboroxime could enhance some of the benefits of the present method. Specifically, with the faster camera systems, the rest and stress scans can be individually completed before most of the Teboroxime clears the heart muscle. On the other hand, the rest tracer may clear significantly between the time it is injected and stress imaging, allowing the second study to be done with relatively little interfering residual activity from the first study.

A benefit of Tc-Sestamibi and Tc-Tetrofosmin is that they remain fixed in the heart for a substantial period of time (i.e. several hours), providing flexibility in the timing of the MPI scan. Also, Tc has a relatively short half-life of six hours, permitting the administration of larger doses (up to 30 mCi) while keeping the amount of radiation imparted to the patient at an acceptable level.

Thallium ("Thallium-210", "Tl", or "210-Tl") is also known in the art to be particularly beneficial for use as the stress radiotracer. The reasons are as follows. First, Thallium uptake in the myocardium increases in tandem with increased blood flow in an essentially linear relationship with almost no practical plateau. Thus, if, under stress, the blood flow through the coronary arteries is five times what it was at rest, a Thallium scan will show almost five times as much activity. This near-linearity holds for all practical differences in myocardial perfusion between rest and stress. This feature is beneficial for a number of reasons, the most important being that it allows accurate comparisons between the blood flows in different parts of the heart muscle.

Other possible stress radiotracers, such as Tc-Sestamibi and Tc-Tetrofosmin, are not taken up in the myocardium in a linear relationship to the increase in blood flow and also tend to plateau. Therefore, as the blood flow begins to increase, tracer uptake increases at a lesser rate. This fall-off in extraction fraction increases with increased blood flow until stress blood flow rises above a certain multiple of the rest blood flow. At this point a plateau is reached and the scan shows the same level of activity regardless of any further increase in the level of coronary blood flow. This can interfere with making accurate comparisons between blood flows in different parts of the heart. Take a case where, under stress, the blood flow in a first part of the heart is markedly lower than the blood flow in a second part, but both blood flow levels exceed the aforementioned multiple. In a Tc-Sestamibi or Tc-Tetrofosmin stress scan, the blood flow will appear the same for both parts of the heart. However, the difference in blood flow between the two parts of the heart could be indicative of a condition that might have been diagnosed and treated if Thallium had been used as the stress radiotracer.

Furthermore, Thallium is taken up by the liver and bowel to a much lesser degree than Tc-Sestamibi, or Tc-Tetrofosmin. Thus, after administering Thallium, there is much less concern about liver and bowel activity interfering with the scan.

There are, however, downsides to using Thallium as the stress radiotracer, which downsides have resulted in Thallium being used rarely as such. First, conventional nuclear medicine Anger cameras are optimized to image the 140 keV gamma rays of Tc-99m and not the main group of lower energy Thallium photons. The lower energy Thallium photons produce fewer light photons per scintillation event, and smaller numbers of light photons result in larger relative statistical fluctuation in their distribution, resulting in a blurry image. In addition, a half-life of approximately 72 hours limits the dose of Thallium that can be administered to a patient, resulting in count-poor studies with relatively blurry images of Thallium distribution. Because of Thallium's longer half-life, a patient should not receive more than 4mCi of Thallium.

Figure 2:
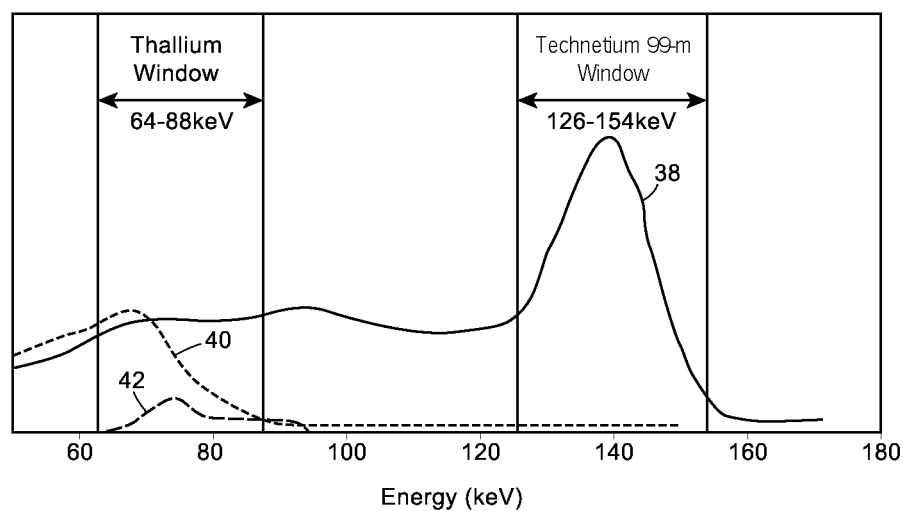
FIG. 2 is an energy spectrum graph for Technetium 99-m and Thallium-201.

An additional problem is crosstalk from the higher energy 140 KeV Tc photons into the lower energy window of Thallium (64-88 keV), due to downscatter and collimator fluorescence. In the prior art methods, when Tc is used as the rest radiotracer, it is typically given at a relatively high dose (10-15 mCi). With conventional Anger cameras, such a dosage would provide a high enough photon count-rate to allow a complete rest MPI scan in about 15 minutes. However, the Tc would remain fixed in the heart, resulting in relatively high intensity cross-talk in Thallium's energy window. In the past this made the use of Thallium as a stress radiotracer impractical. FIG. 2 shows the energy spectrum for Tc-99m (reference numeral 38), the energy spectrum for Tl-201 (reference numeral 40) and the energy spectrum for downscatter and of lead fluorescence x-rays resulting from Tc-99m photons interacting with the lead collimator of the SPECT camera (reference numeral 42). As can be seen from FIG. 2, items 38 and 42 represent the relatively high intensity Tc-crosstalk in the Thallium energy window 40.

One way to avoid the problem of cross-talk into Thallium's energy window would be to perform the stress scan first, using Thallium as the stress radiotracer, as discussed below in relation to the alternative embodiment. However, it will be appreciated that performing the stress scan before the rest scan creates the possibility of a false resting abnormality caused by occasional unusually persistent ischemia following earlier stressing.

As discussed above, in one embodiment of the present invention, Tc is used as the rest radiotracer, and Thallium as the stress radiotracer. In this embodiment, it is possible to perform the rest MPI scan so that it starts when the rest radiotracer is fixed in the heart, and continues all the way through the administration of the stressing agent, the administration of the stress radiotracer, a brief delay for complete myocardial uptake and the performance of the stress MPI scan. Scanning Tc and Tl at the same time is known as Simultaneous Dual-isotope Imaging (SDI). If rest imaging is to continue after injection of Thallium, there is potential for downscatter contamination by the Tl gammas at 135.3 and 167.4 keV into the 140 keV Tc window. Fortunately these are in low abundance, but depending on how low the dose of Tc is relative to Tl, some correction may be advisable. In particular, this embodiment employs a much lower ratio of Tc to Tl than previously envisioned, as described below. With more time available to complete the rest MPI scan, using a fast camera system it is practical to administer Tc as the rest radiotracer at a dose as low as 3 to 5 mCi. At this lower dose, a greater amount of time (approximately 15 minutes on current CZT cameras), will be needed to get a high enough photon count to complete the scan. At the Tc lower dose, the Tc-crosstalk in Thallium's energy window will be of much lower intensity, making it more practical to use Thallium as the stress radiotracer, perhaps in conjunction with other SDI compensation techniques. An additional benefit of using a lower dose of Tc as the rest radiotracer is that the total amount of radiation imparted to the patient is reduced.

As explained above, using a very low dose of Tc as the rest radiotracer facilitates the use of Thallium as the stress tracer, because at such a low dose the intensity of the Tc crosstalk is low enough so as not to substantially affect the Thallium stress MPI scan images. However, the Thallium-based stress scan image can be improved further by eliminating or minimizing the effect of the residual Tc crosstalk. This can be done by taking a pre-stress-scan image in the Thallium energy window immediately before the Thallium is administered. That image reflects the crosstalk from the Tc. Then, once the Thallium is administered and the stress scan taken, the crosstalk as recorded in the pre-stress scan image can be subtracted from the stress Tl scan image to produce a refined stress image virtually free of Tc crosstalk. The ability to directly measure the Tc crosstalk before subtracting it from the Thallium image in an individual patient follows from the fact that in the preferred form of the present method, the patient is not moved between stress and rest studies, which are done in rapid succession and the fact that Tc imaging is started before Tl imaging, unlike currently proposed SDI protocols. In currently-proposed SDI protocols, both rest and stress injections are completed before the start of imaging and therefore complicated mathematical modeling is necessary to estimate Tc crosstalk, since it is not directly measurable in the presence of Tl. Thus the ability to directly estimate and subtract Tc crosstalk from the Thallium stress scan will also facilitate SDI. Incidentally, it will be appreciated that unlike the present method, "standard" SDI allows for only one GSPECT study, which limits the information that can be derived from a scan, in that transient ischemic dilation and dysfunction are not assessed.

It will be appreciated that the method of the present invention is most preferably carried out using newer, faster, SPECT nuclear medicine technologies, including cameras employing CZT detectors. In addition to their great speed, these cameras create much better Tl images than standard Anger scintillation cameras. CZT cameras also have much better energy resolution than older cameras, giving them a distinct advantage in the area of SDI.

As mentioned above, in the preferred embodiment, the step 28 (administering the stressing agent) will commence shortly after the rest perfusion scan has begun (step 26) so that the stress GSPECT can be obtained (step 30). The reason for this is that it keeps the patient under the camera for less time. Because the present method uses the rest radiotracer to obtain stress GSPECT, the rest perfusion imaging (step 26) can overlap with the administration of the stressing pharmaceutical (step 28) and the stress GSPECT (step 30). Furthermore, because the rest perfusion scan (step 26) can overlap with steps 28 and 30, more time can be allotted to the rest perfusion scan (step 26) while still shortening the total time that the patient is under the camera. This, in turn, allows lower doses of radiopharmaceutical to be administered to the patient, since more time is available to obtain the photon counts necessary for an adequate perfusion scan, with the result that less total radiation is imparted to the patient and staff.

On the other hand, there is a theoretical possibility of partial volume artifact (PVA) resulting from the stressing agent's inducing a false resting perfusion defect in an area of normal resting perfusion. This possibility arises from the fact that the radioactivity emitted from the radiopharmaceutical fixed in the heart is proportional to the mass of muscle per unit volume, and the fact that under stress, ischemic myocardium may stretch and thin out. If the stressing agent is administered before rest perfusion imaging is completed, there may theoretically be less lesion contrast between the rest and stress perfusion images than there should be. While it is believed that PVA is highly unlikely and its possibility can be ignored, the possibility of PVA can be eliminated entirely by acquiring the entire rest perfusion scan (step 26) before stress agent administration (step 28), though doing so would take more time than overlapping the steps.

As mentioned above, prior art protocols using conventional Anger cameras have often called for a delay of at least 30-45 minutes between the administration of a radiotracer and the corresponding MPI scan. The reason is that the radiotracer may immediately accumulate the liver and progress from there to the bowel. Because of the position of the liver, and of some bowel loops, radiotracer in the liver and bowel could interfere with the imaging of the heart.

It has been found that interference from the liver and bowels is less of a problem today than previously believed, for several reasons. First, algorithms for creation of the SPECT image have improved. Now, even conventional Anger cameras often use iterative reconstruction algorithms to generate the SPECT image. It has been found that as compared to the older method of filtered back-projection, iterative reconstruction tends to reduce the practical effect of liver interference, to the point where valid results are almost always obtained without waiting for the radiotracer to clear the liver. Newer CZT SPECT cameras all use iterative reconstruction.

Second, while the radiotracer accumulates in the liver almost immediately, it takes substantially longer to transit into and through the bowel. It will usually be possible, in accordance with the present invention, to complete both the rest and stress MPI scans before either radiotracer enters the bowel to a significant degree. In rare cases where extra cardiac activity does interfere with the stress scan, the patient can be asked to return for stress imaging at a later time. The decision to return for a repeat stress scan would be done immediately after the stress scan is completed, either by a physician who is present, or the technologist. Even with this delay, the whole study would be completed in a time that is less than or equal to the prior art.

It will be appreciated that the rest radiotracer may comprise Thallium, and the stress radiotracer a Technetium-based radiopharmaceutical. A benefit of such an approach is the very low likelihood of activity from the rest injection transiting to the bowel by the time of the stress scan. (As described above, because of the increased speed of newer cameras, there is an even lower likelihood of activity from the stress injection transiting to the bowel by the time of the stress scan.) Such an approach would also eliminate the need for SDI techniques, since the Thallium is imaged before, and not after, the Technetium.

It will also be appreciated that Thallium may be used as both the rest and stress radiotracer, as may Technetium based radiopharmaceuticals. In both of these cases, the first radiotracer administered would be given at a lower dose than the second radiotracer administered.

It will be appreciated that the present method has the potential to expand the practical usefulness of SPECT to new areas. For example, it is common for patients with chest pain, or other possible symptoms of heart attack or heart disease, to arrive at the emergency room of a hospital seeking treatment. Such patients may be given an ECG, and have other conventional ER diagnostic techniques performed on them. Acute chest pain MPI protocols, which patients undergo in order to rule out ischemia, have been successfully introduced in many emergency departments and have been proven to be cost effective. It is likely that acute chest pain MPI will gain even wider acceptance, once a significant reduction in scan time is realized. Safety will be increased by having the patient spend much less time out of the Emergency Department and result turnaround time will improve dramatically.

One problem that sometimes arises in SPECT imaging is patient movement. If the patient moves during the scan, the image, which would otherwise be clear, comes out blurry. Furthermore, the image may well be misleading, as various parts of the heart muscle may appear to have better or worse perfusion than they really do.

With conventional Anger cameras, a typical MPI scan usually involves approximately 60 planar images taken successively at different angles. Patient movement can be easily observed by a shift in position between successive images. Simple up-down or side-to-side motion can be corrected by computer methods which shift the weighted center of the heart on post-movement images to align them with the pre-movement images.

By contrast, with the newer CZT cameras that are now in use, there has been no easy way to detect, let alone correct, patient motion during the scan. The reason is that with these new cameras, the raw images from which the SPECT scan is created are not organized according to time. With some CZT cameras, such as the Discovery 530c produced by GE, each of the 19 raw pinhole images lasts for the entire duration of the scan. With Spectrum Dynamics' D-SPECT there are just two successive scans, each lasting half of the entire scan time. Each of the two half-scans is created by the sum of scans from multiple heads. These heads rotate in different directions and times in relation to the other heads, so that there is no temporal organization of the components of each half-scan.

Thus, preferably, the method comprises performing multiple consecutive short perfusion scans, whether rest or stress, and storing the data associated with each short scan separately. Typically, each these short scans would lack the high photon count required for perfusion images used for diagnosis. However, the data from the multiple short scans can be combined to produce at least one single high-photon-count perfusion scan suitable for diagnosis.

It will be appreciated that the multiple consecutive short scans can be used to detect and correct patient motion. Specifically, these scans, having been performed one after the other, can be used to determine whether the patient moved, how the patient moved (up-down, side-to-side) and approximately when the patient moved. This information could then be used to correct for patient motion during scans done using CZT cameras, or any camera system where images are not intrinsically temporally organized. The multiple images from the short scans would be combined for a high count (and if necessary, motion-corrected) perfusion image.

For CZT cameras with moving head assemblies, such as the Spectrum Dynamics camera, the multiple short scans could be performed by speeding up cycling, such as to their published maximum velocity of 10 seconds. With cameras such as GE's Discovery 530c that employ immobile detectors, implementation of this technique is even easier. The image may be initially acquired in separate bins, the number of which is limited only by practical considerations of having enough counts to see the myocardium. If the study is acquired in list-mode, then the images may be binned after scanning. Alternatively instead of using reconstructed SPECT images for motion detection and correction, raw images may be employed. In the case of stationary detector CZT cameras such as the GE camera, multiple scans can be performed by periodically ending a short scan and beginning the next one. Each of the short scans should be long enough to acquire a recognizable, statistically valid image, but short enough to have good temporal resolution in order to catch the motion close to the time it occurs. In the case of a moving detector system like the D-SPECT, although images generated from each camera head assembly translational position are only a partial images, these partial images can still be used to detect patient movement. With both cameras the duration of the short scans could be chosen in advance, or the intervals may be set retrospectively by taking advantage of list mode acquisition.

It will be appreciated that one or more of the multiple short scans can comprise a GSPECT image. As mentioned above, GSPECT does not require the same high-photon-count, statistically smooth image that a perfusion scan does. Thus, it can be reacquired multiple times as part of the performance of multiple short scans. If one or more of the multiple short scans is used for GSPECT, then the data from those same scans can be combined to create the perfusion image, while the gated data can be used to assess heart pumping ability, including wall motion and left ventricle ejection fraction at various time intervals. Performing multiple GSPECT studies may be advantageous from a diagnostic perspective.

Figure 3:
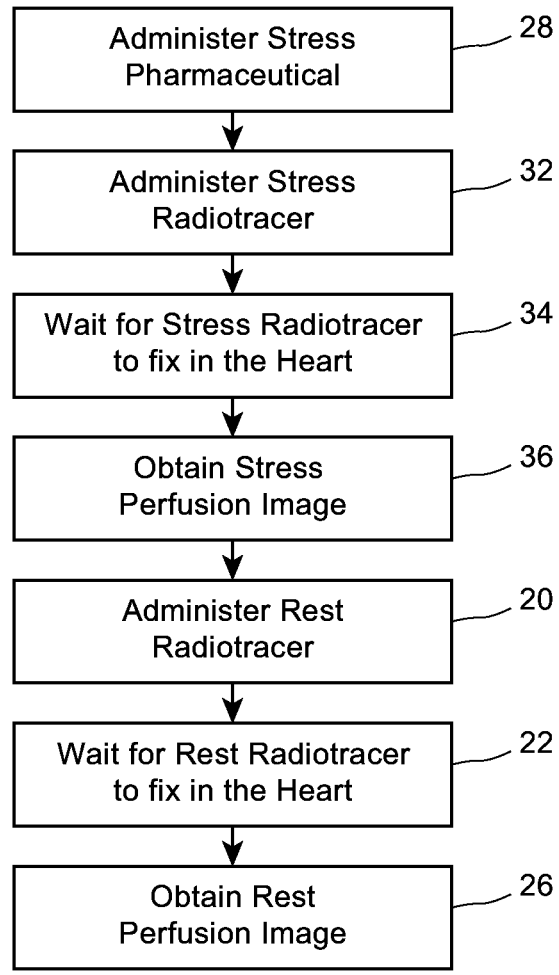
FIG. 3 is a flowchart showing an alternate embodiment of the method.

In an alternate embodiment (see FIG. 3), the stress scanning may be performed before the rest scanning Thus, after a stress agent is administered, and a stress radiotracer administered and fixed in the heart, stress scanning as described above is performed. The sooner scanning is commenced, the higher the likelihood or catching transient ischemic LV dilation, or dysfunction. Most preferably (though not necessarily) without moving the patient, the rest radiotracer is then administered, and once fixed in the heart, rest scanning as described above is performed. This alternate also allows the stress heart pumping ability information to be obtained at or near peak stress. In this alternate embodiment, the rest radiotracer and stress radiotracer may be the same, with the second (rest) radiotracer being given at a higher dose, as described above. Or, the first (stress) radiotracer may comprise a technetium-based radiopharmaceutical, and the second (rest) radiotracer Thallium, or vice versa, as described above. The specifics and variations described above in relation to the main embodiment may be applied, mutatis mutandis, to the alternate embodiment.

In the main embodiment described in detail above, stress agents that involve moving the patient (e.g. treadmill exercise) are not preferred because it is desirable not to move the patient between the rest and stress scans. Therefore, a benefit of this alternate embodiment is that the stressing agent is administered before the patient is placed under the camera, and then the stress and rest scan are performed in succession with, or without further movement of the patient. Thus, in the alternate embodiment, a stressing agent that involves moving the patient (e.g. treadmill exercise) can be usefully employed, yet GSPECT can be performed before LV dilation and dysfunction have a chance to recover from stress.

On the other hand, in this alternate embodiment, there is some risk that the rest perfusion and heart pumping ability images will be somewhat contaminated by the relatively recent stress procedure. The reason is that it is possible that by the time the rest radiotracer is administered (typically 5-10 minutes after peak stress), perfusion has not yet returned to their normal (rest) state. Furthermore, it is possible that even by the time of rest imaging, cardiac size and function would not return to normal. However, it is believed that in that 5-10 minute period, perfusion will generally return to normal and that in the few more minutes used to scan the heart, LV size and function will generally return to normal, in the sense that they would be significantly improved as compared with peak stress.

It will be appreciated that the alternate embodiment complements the main embodiment, in that both embodiments comprise methods that can be completed in single twenty-minute slots with appropriate cameras, and can provide superior GSPECT and image correlation, as compared with the prior art.

Referring now to another aspect of the invention, it is known by those skilled in the art that a diagnostically valid SPECT image requires an adequate photon count. In the field of SPECT, there is often a trade-off between, on the one hand, obtaining a sufficient number of counts for diagnostic validity, and on the other hand, conducting the imaging within an acceptably short time and imparting to the patient an acceptably low dose of radiation.

In nuclear cardiology, to obtain a diagnostically valid image, it is known to image the left ventricle ("LV") for a set number of counts, instead of the older method of scanning for a set time period. Imaging for a set number of counts corrects for the fact that different patients have different count rates (i.e. a different number of counts per unit of time). Patients' count rates differ for various reasons. For example, photons are absorbed or attenuated by tissues from their origin within the body en route to the detector, with the absorption and attenuation depending on the amount and composition of tissues along that route. That in turn depends on the size and shape of the particular patient. Also, the percentage of the tracer dose taken up in the LV varies from patient to patient. Furthermore, the amount of radioactivity drawn into the syringe before the tracer is injected is variable, as is the quantity of radioactivity left behind in the syringe after the injection. There is also variation in the time between tracer injection and imaging, during which the tracer decays. Scanning until a set number of LV photon counts is reached corrects for this variability in count rates.

The assumption underlying this approach is that there is a generalized minimum number of LV counts sufficient to create a valid diagnostic image. "Generalized" means that the minimum number is the same, or essentially the same, for all patients. Contrary to this assumption, however, it is advantageous when performing LV scans to scan for a set number of photon counts per unit volume of LV tissue. The reason is that, to obtain a diagnostically valid image, an adequate number of counts is needed from all areas of the LV for image uniformity. A larger LV will require a higher total of LV counts than a smaller LV to obtain image uniformity, because the available counts from a larger LV are distributed over a greater volume. Thus, the best use of scanning time and/or radiation imparted to the patient is to scan for a particular, predetermined, number of LV counts per unit volume of LV. It is possible that the ideal number of counts per unit of LV volume required for a diagnostic scan may vary somewhat due to factors such as patient size. This would require a hybrid approach where the required number of counts per unit volume of LV would be adjusted by other factors, such as patient size.

In the context of SPECT imaging, units of volume are represented by volumetric pixels, or voxels. Thus, in this aspect of the invention, the SPECT imaging scan would be set to continue until a predetermined number of counts per voxel is reached.

Preferably, the predetermined number of counts per voxel comprises a threshold count number ("TCN") that is selected so that adding more counts to the TCN will not significantly improve the quality and diagnostic validity of the scan, but subtracting counts from the TCN would appreciably degrade the quality of the scan. It will be appreciated that the TCN exists in a definable range, and varies according to the imaging equipment being used. For any particular type of imaging equipment, the TCN's range can be determined by running actual scans in list-mode. Images can be retrospectively created and saved at fractions of original scan times at different possible TCNs. By inspection, it would be possible to determine the range of the TCN for the particular type of imaging equipment.

It will be appreciated that using a TCN will allow the minimization of scanning time and/or radiation dose, because the TCN is the lowest count number per voxel that still provides substantially the highest possible quality image. In addition, different imaging systems can be compared by determining the time to reach the TCN of each. In essence, the threshold count number of an imaging system is a measure of its efficiency in producing diagnostically valid images—the lower the time to reach the TCN, the lower the scan time and/or radiation dose necessary to produce a diagnostically valid image.

It will be appreciated that this method of scanning to a predetermined number of counts per unit volume or voxel can be applied, mutatis mutandis, to other tissues or organs of the body besides the heart.

In previously-described embodiments, rest and stress LV ejection fraction information is obtained once the respective rest and stress radiotracers are fixed. In an alternate embodiment, measurements of LV volume and LV ejection fraction are performed without waiting for the radiotracer to fix in the heart muscle.

There are two main ways of measuring LV volume and ejection fraction. The first, mentioned above, is to acquire multi-gated perfusion images of the movement of the myocardium (i.e. the walls of the heart, or heart muscle). Such images can be obtained once the radiotracer is fixed in the heart, providing an image of the movement of the myocardium. Volume and ejection fraction can be measured by measuring the "empty space" in the image that represents the volume of the left ventricle within the myocardium, in the LV's expanded and contracted positions.

The second is the performance of early imaging, otherwise known as a first pass study. In a first pass study, imaging does not wait for the radiotracer to become fixed in the muscle. Rather, immediately upon the infusion of the radiotracer into the patient, the "first pass" of the blood-borne radiotracer through the LV is imaged. The image provided is therefore not an image of the myocardium, but rather, an image of the blood within the LV (containing the radiotracer). As the LV expands and draws in tracer-infused blood, an image is taken to show LV volume at the LV's expanded position. When the LV contracts to pump the blood to the body, the volume of the LV is again measured. The difference between the two volumes is used to calculate the ejection fraction.

Different existing CZT cameras have different capabilities in relation to early imaging. It has been found that Spectrum Dynamics' D-SPECT camera can do a first pass image of the heart within one minute of injection of a Tc-tracer (such as Tc-Sestomibi or Tc-Tetrofosmin) Neither blood pool activity nor liver activity appears to interfere with such imaging.

Regarding the existing GE Discovery 530c camera, it has been found the scans done within the first few minutes of Tc-tracer injection are often un-interpretable. Even after about 10 minutes, when blood pool activity has cleared, there is often poor definition in the images. It is believed that these effects are the result of liver activity. In particular, the 530c uses three rows of pinhole detectors to obtain the image. The lowest row of detectors looks up at the heart with a few detectors looking up through the liver, so that liver activity would interfere with imaging of the heart.

To avoid this problem with the 530c, a modification could be made to the camera. The 530c has three rows of nine potential pinholes each. In each of the top and bottom rows, only five of the pinhole positions are active. It is believed that if the active pinholes on the bottom row are rearranged, so that the two pinhole detectors in the lowest row furthest to the right (i.e. closest to the patient's liver) are moved to unused spaces in the bottom row or upper row, then the 530c would be able to reliably do early imaging of the heart. With such a modification, it would be necessary to make a corresponding modification to the reconstruction algorithm. It is believed that this modification to active pinhole positions would not have a substantial negative impact on camera performance.

It will be appreciated that while liver activity is associated with Tc radiotracer, splanchnic activity does not occur to a significant degree when Thallium is used as the radiotracer. Thus, both the current 530c camera and the D-SPECT camera can image Thallium within about one minute of injection, and blood pool activity does not significantly degrade these images.

It will be appreciated that there are advantages to employing first pass imaging for the rest and/or stress scans. First, the amount of time that must pass before a stressing agent is administered is reduced. Specifically, in some of the embodiments described above, the stressing agent is not administered until a resting gated myocardial perfusion image (GMPI), resting LVEF and resting LV volume (LVV) are obtained. In those embodiments, resting GMPI, LVEF and LVV can't be started until the tracer fixes in the heart and pharmacological stress cannot start until resting GMPI is completed. In this alternate embodiment, LVEF and LVV (and possibly wall motion images) are obtained during the first one or two passes of the radiotracer through the heart (whether at rest or under stress). Thus, resting LVEF and LVV data can be obtained within seconds of radiotracer injection, and the stress agent can be administered with 1-2 minutes of rest radiotracer injection, just enough time for the rest radiotracer to become fixed in the myocardium.

The first pass radiotracer need not be the same as the myocardial perfusion imaging agent, although in most cases it will be, in order to minimize the amount of radioactivity injected. On the other hand a different tracer with a short physical and/or biological half-life could be used for the 1st pass studies.

Thus, in this embodiment, an example protocol might proceed as follows. Tc radiotracer is injected as the rest radiotracer, and within seconds, a first pass study is completed, showing resting LVV and LVEF. After 1-2 minutes, Persantine is then infused over about 4 minutes, and a subsequent standard delay of at least 3 minutes passes before the Thallium stress radiotracer is injected. As soon as the Tc is fixed in the heart, the rest imaging is commenced until completion. Similarly, as soon as the Thallium is fixed in the heart, the stress imaging is commenced until completion. As discussed above, the rest and stress imaging may overlap in such a protocol, since Thallium and Tc can be imaged simultaneously. Also, because Tc and Thallium can be imaged simultaneously, the rest perfusion imaging does not interfere with or impede a Tl stress first pass study. Although there is plenty of time to acquire a GMPI stress scan using Tc rest radiotracer (or even the Tl stress radiotracer), it may be preferable to perform a first pass stress study to best compare with the first pass rest study. Furthermore, as discussed above, before the administration of Thallium, an image of the Tc activity in the Thallium energy window can be taken, and that image subtracted from the subsequent Thallium stress image. To save time, using list mode, the Tc-activity-in-Tl-window scan can be obtained simultaneously with the rest myocardial perfusion scan, as opposed to obtaining that image separately.

To increase further the time saving benefits of the invention, a faster acting and more quickly-administered stress agent can be employed. An example of such an agent is Regadenoson. Regadenoson is practical for MPI, because it can produce the required vasodilation through a single injected dose, rather than infusion over a period of time, and once administered it also acts more quickly than Persantine does.

It will be appreciated by those skilled in the art that the method of using first pass studies, as described herein, can be applied, mutatis mutandis, to any embodiment of the invention.

Dynamic imaging has the potential to increase the diagnostic power of myocardial perfusion scanning by providing absolute blood flow measurements. Among other advantages, this could help diagnose cases of balanced 3-vessel CAD, a dangerous condition that is often difficult to diagnose using traditional myocardial perfusion imaging. Dynamic imaging requires short, sequential images of the heart to be acquired shortly after, or immediately after, injection, in order to calculate input and output functions, for a compartment model. Historically, this has been considered possible only with PET but not SPECT, because only PET was able to acquire rapid sequential 3-dimensional images. CZT cameras are among the first SPECT systems able to acquire a complete 3-dimensional dataset in several seconds or less, giving them the potential to provide absolute perfusion information that can be used to diagnose balanced 3-vessel CAD, as opposed to merely relative perfusion information of current MPI techniques. The first pass injection embodiment of the rapid imaging protocol described in this application requires the patient to be injected with radiotracer while on the table, followed shortly thereafter by imaging the patient in the same position. Adding dynamic SPECT imaging to this protocol, therefore, requires little additional logistical effort on the part of staff or patient. Therefore, the protocol described above greatly enhances the feasibility of performing quantitative dynamic imaging. In addition, reconfiguring the pinholes on the Discovery 530c camera as described above may help it achieve the promise of dynamic quantitative imaging more easily, by eliminating confounding gut activity overlapping the inferior wall that is common on images taken shortly after injection of Tc radiotracer.

While the foregoing preferred embodiments of the present invention have been set forth in considerable detail for the purpose of making a complete disclosure of the invention, it will be apparent to those skilled in the art that other embodiments described herein are comprehended by the broad scope of the invention as defined in the attached claims.

The invention claimed is:

1. A SPECT diagnostic method of performing myocardial perfusion imaging on a patient, the method comprising the steps of:
   (A) administering a stressing agent to the patient to place the patient's heart under stress; then
   (B) administering a stress radiotracer while the heart of the patient is under stress;
   (C) when the stress radiotracer is fixed in the heart, immediately scanning the heart to obtain a stress perfusion image and stress heart pumping ability information;
   (D) administering a rest radiotracer to the patient once the patient is at rest, the rest radiotracer and stress radiotracer comprising the same radiopharmaceutical, with the rest radiotracer being administered at a higher dose than the stress radiotracer;
   (E) when the rest radiotracer is fixed in a heart of the patient, scanning the heart to obtain rest heart pumping ability information and a rest perfusion image;
   (F) subtracting the stress perfusion image from the rest perfusion image to obtain a refined rest perfusion image.

2. The SPECT diagnostic method as claimed in claim 1, wherein the rest and stress radiotracers both comprise a Technetium-based radiopharmaceutical.

3. The SPECT diagnostic method as claimed in claim 2, wherein said step (B) comprises administering 5 mCi or less of Technetium to the patient.

4. The SPECT diagnostic method as claimed in claim 1, wherein the rest and stress radiotracers both comprise Thallium.

5. The SPECT diagnostic method as claimed in claim 1, wherein the stressing agent comprises a stress pharmaceutical which is selected from the group consisting of dipyridamole, dobutamine, adenosine, and regadenosone.

6. The SPECT diagnostic method as claimed in claim 1, wherein the stressing agent comprises a non-pharmaceutical stressing agent.

7. The SPECT diagnostic method as claimed in claim 6, wherein the non-pharmaceutical stressing agent is selected from the group consisting of cold presser testing, mental stress, bicycle exercise, and handgrip exercise.

8. The SPECT diagnostic method as claimed in claim 7, wherein the patient remains in a scanning position from step (C) through step (E) inclusive.

9. The SPECT diagnostic method as claimed in claim 1, wherein the patient remains in a scanning position from step (C) through step (E) inclusive.

* * * * *

UNITED STATES PATENT AND TRADEMARK OFFICE
CERTIFICATE OF CORRECTION

PATENT NO.       : 9,517,037 B2
APPLICATION NO.  : 14/877142
DATED            : December 13, 2016
INVENTOR(S)      : Bienenstock Page 1 of 1

It is certified that error appears in the above-identified patent and that said Letters Patent is hereby corrected as shown below:

In the Claims

Column 17, Line 14, Claim 1, after "heart," delete "immediately"

Column 18, Line 13, Claim 5, delete "regadenosone." and insert -- regadenoson. --

Signed and Sealed this
Seventh Day of March, 2017

Michelle K. Lee
*Director of the United States Patent and Trademark Office*